US010835644B2

(12) United States Patent
Minagawa et al.

(10) Patent No.: US 10,835,644 B2
(45) Date of Patent: Nov. 17, 2020

(54) SURFACE-MODIFIED METAL AND METHOD FOR MODIFYING METAL SURFACE

(71) Applicant: SUMITOMO RUBBER INDUSTRIES, LTD., Kobe (JP)

(72) Inventors: Yasuhisa Minagawa, Kobe (JP); Takefumi Nakashita, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 350 days.

(21) Appl. No.: 14/771,116

(22) PCT Filed: Oct. 8, 2014

(86) PCT No.: PCT/JP2014/076893
§ 371 (c)(1),
(2) Date: Aug. 27, 2015

(87) PCT Pub. No.: WO2015/056611
PCT Pub. Date: Apr. 23, 2015

(65) Prior Publication Data
US 2016/0008520 A1    Jan. 14, 2016

(30) Foreign Application Priority Data

Oct. 18, 2013  (JP) ................................. 2013-217564
Apr. 18, 2014  (JP) ................................. 2014-086587

(51) Int. Cl.
| | | |
|---|---|---|
| *A61L 31/10* | (2006.01) | |
| *C09D 4/00* | (2006.01) | |
| *A61L 31/02* | (2006.01) | |
| *A61L 31/14* | (2006.01) | |
| *B05D 1/18* | (2006.01) | |
| *B05D 3/06* | (2006.01) | |
| *C08F 220/38* | (2006.01) | |
| *C08F 2/48* | (2006.01) | |
| *C08F 2/50* | (2006.01) | |

(52) U.S. Cl.
CPC .............. *A61L 31/10* (2013.01); *A61L 31/022* (2013.01); *A61L 31/14* (2013.01); *B05D 1/18* (2013.01); *B05D 3/067* (2013.01); *C09D 4/00* (2013.01); *A61L 2400/10* (2013.01); *A61L 2400/18* (2013.01); *A61L 2420/02* (2013.01); *C08F 2/48* (2013.01); *C08F 2/50* (2013.01); *C08F 220/38* (2013.01)

(58) Field of Classification Search
CPC .............. C08F 22/10; A61L 31/10; C08K 5/05
USPC .......................................................... 526/318
See application file for complete search history.

(56) References Cited

U.S. PATENT DOCUMENTS

| | | | |
|---|---|---|---|
| 3,532,655 A | | 10/1970 | Radlove et al. |
| 5,218,070 A | * | 6/1993 | Blackwell ............ A61K 6/0023 523/113 |
| 5,693,034 A | * | 12/1997 | Buscemi ................ A61L 29/085 424/486 |
| 6,001,894 A | | 12/1999 | Ottersbach et al. |
| 6,013,855 A | | 1/2000 | McPherson et al. |
| 6,221,425 B1 | * | 4/2001 | Michal ................... C08L 89/00 427/2.25 |
| 6,391,463 B1 | | 5/2002 | Fan et al. |
| 9,695,331 B2 | | 7/2017 | Horgan et al. |
| 2003/0215649 A1 | | 11/2003 | Jelle |
| 2006/0013853 A1 | | 1/2006 | Richard |
| 2008/0300573 A1 | * | 12/2008 | Consigny ................ A61L 27/54 604/509 |
| 2009/0020431 A1 | * | 1/2009 | Voccia ................ B81C 1/00206 205/77 |
| 2009/0171302 A1 | | 7/2009 | Eramo et al. |
| 2009/0178183 A1 | | 7/2009 | Conrad et al. |
| 2010/0145286 A1 | | 6/2010 | Zhang et al. |
| 2011/0027757 A1 | | 2/2011 | Kyomoto et al. |
| 2011/0059874 A1 | | 3/2011 | Rooijmans et al. |
| 2011/0212152 A1 | | 9/2011 | Ditizio et al. |

(Continued)

FOREIGN PATENT DOCUMENTS

| | | |
|---|---|---|
| CN | 101970583 A | 2/2011 |
| CN | 103209717 A | 7/2013 |

(Continued)

OTHER PUBLICATIONS

E1, Fusion UV 558439 Equivalent 6" H Type UV Lamp, 2019, cureuv.com, https://www.cureuv.com/products/electrodeless-6-h-300-wpi-ozone-free-uv-lamp (Year: 2019).*

(Continued)

*Primary Examiner* — Dah-Wei D. Yuan
*Assistant Examiner* — Andrew J Bowman
(74) *Attorney, Agent, or Firm* — Birch, Stewart, Kolasch & Birch, LLP.

(57) ABSTRACT

The present invention provides surface-modified metals such as metal medical devices, e.g., guide wires, syringe needles, and metal tubes in medical devices or equipment, in which a lubricant layer is firmly bonded to the surface to impart lubricity to the surface, and further to improve the durability of the lubricant layer on the surface, thereby reducing deterioration of sliding properties, as well as methods for modifying a metal surface. The present invention relates to a surface-modified metal having a surface at least partially treated by polymerizing a monomer in the presence of a hydrogen abstraction type photopolymerization initiator.

3 Claims, No Drawings

(56) References Cited

U.S. PATENT DOCUMENTS

| | | |
|---|---|---|
| 2012/0059111 A1 | 3/2012 | Sandhu et al. |
| 2013/0242467 A1 | 9/2013 | Biler |
| 2013/0266815 A1 | 10/2013 | Horgan et al. |
| 2016/0008520 A1 | 1/2016 | Minagawa et al. |
| 2016/0159019 A1 | 6/2016 | Bruce et al. |
| 2016/0184487 A1 | 6/2016 | Minagawa |
| 2017/0056563 A1 | 3/2017 | Minagawa |

FOREIGN PATENT DOCUMENTS

| | | |
|---|---|---|
| EP | 0872512 A2 | 10/1998 |
| GB | 1065031 A | 4/1967 |
| JP | 60-179204 A | 9/1985 |
| JP | 62-52562 A | 3/1987 |
| JP | 2-40322 A | 2/1990 |
| JP | 4-357951 A | 12/1992 |
| JP | 4-362104 A | 12/1992 |
| JP | 5-269919 A | 10/1993 |
| JP | 6-510322 A | 11/1994 |
| JP | 8-325524 A | 12/1996 |
| JP | 2001-29452 A | 2/2001 |
| JP | 2005-528253 A | 9/2005 |
| JP | 2011-513566 A | 4/2011 |
| JP | 2013-538247 A | 10/2013 |
| WO | WO 03/097117 A1 | 11/2003 |
| WO | WO 2005/081840 A2 | 9/2005 |
| WO | WO 2006/056482 A1 | 6/2006 |
| WO | WO 2009/081870 A1 | 7/2009 |
| WO | WO 2012/006135 A2 | 1/2012 |
| WO | WO 2012/032283 A1 | 3/2012 |

OTHER PUBLICATIONS

International Search Report, issued in PCT/JP2014/076893, dated Dec. 22, 2014.

Written Opinion of the International Searching Authority, issued in PCT/JP2014/076893, dated Dec. 22, 2014.

* cited by examiner

SURFACE-MODIFIED METAL AND METHOD FOR MODIFYING METAL SURFACE

TECHNICAL FIELD

The present invention relates to surface-modified metals and methods for modifying a metal surface.

BACKGROUND ART

Guide wires and the like used for assisting insertion of a medical device, such as a catheter, into the body are inserted into and optionally placed in blood vessels, respiratory tracts, urethra, and other body cavities or tissues in some cases. When such a medical device as a catheter or guide wire is inserted into the body, the medical device may damage the tissue or the like in the body and produce inflammation or cause pain to the patient. To ameliorate these problems, it has been desired to improve the sliding properties of the medical devices to be inserted into the body.

To ameliorate the above problems, a method has been proposed in which the surface of a medical device such as a catheter or guide wire is coated with a hydrophilic resin, a fluororesin or the like.

Moreover, the insertion of a syringe needle into the body may also damage the tissue or the like in the body and cause pain to the patient.

Furthermore, if the inner surface of a syringe needle, a metal tube in a medical device or equipment, or the like has reduced lubricity when in a wet condition, then there may be difficulties in rapidly and accurately delivering chemicals or blood. Thus, it has been desired to improve and maintain the lubricity of the inner surface in a wet condition.

SUMMARY OF INVENTION

Technical Problem

As described above, there have been needs to improve the sliding properties of medical devices and syringe needles, and to improve and maintain the lubricity of the inner surface of syringe needles, metal tubes in medical devices or equipment and the like in a wet condition. Various methods have therefore been tried to impart lubricity to the surface of medical devices such as catheters and guide wires to improve the sliding properties thereof.

However, all the methods only allow the surface of medical devices to be coated with a resin or to be cured after the coating. Especially in the case where the surface of the medical device is made of a metal, since the coating resin is not firmly bonded to the surface of the medical device, it can be easily peeled or removed from the surface of the medical device, with the result that unfortunately the sliding properties of the medical device are deteriorated. Accordingly, the development of metal medical devices in which deterioration of sliding properties is reduced has been desired. In addition, there is still room for improvement in improving and maintaining the lubricity of the inner surface of syringe needles, metal tubes in medical devices or equipment, and the like in a wet condition.

The present invention aims to solve the above problems and provide surface-modified metals such as metal medical devices, e.g., guide wires, syringe needles, and metal tubes in medical devices or equipment, in which a lubricant layer is firmly bonded to the surface to impart lubricity to the surface, and further to improve the durability of the lubricant layer on the surface, thereby reducing deterioration of sliding properties, as well as methods for modifying a metal surface.

Solution to Problem

The present invention relates to a surface-modified metal, having a surface at least partially treated by polymerizing a monomer in the presence of a hydrogen abstraction type photopolymerization initiator.

The hydrogen abstraction type photopolymerization initiator is preferably present as an adsorbate on the surface.

The surface is preferably treated with a silane coupling agent prior to polymerizing the monomer in the presence of the hydrogen abstraction type photopolymerization initiator.

The surface is preferably further treated, after polymerizing the monomer in the presence of the hydrogen abstraction type photopolymerization initiator, by polymerizing a monomer at least once in the presence of a hydrogen abstraction type photopolymerization initiator optionally present as an adsorbate on the surface.

The monomer is preferably at least one selected from the group consisting of hydrophilic monomers and metal salt-containing hydrophilic monomers.

The silane coupling agent is preferably a vinyl group-containing compound.

The surface-modified metal preferably includes stainless steel or a nickel-titanium alloy.

The present invention also relates to a medical device, including the surface-modified metal.

The medical device is preferably a guide wire, a syringe needle, or a tube of a medical instrument.

The present invention further relates to a method for modifying a metal surface, including the step of growing polymer chains on the metal surface by polymerizing a monomer in the presence of a hydrogen abstraction type photopolymerization initiator on the metal surface.

The method preferably includes the step of treating the metal surface with a silane coupling agent prior to the step of growing polymer chains.

The method preferably further includes, after the step of growing polymer chains, the step of polymerizing a monomer at least once in the presence of a hydrogen abstraction type photopolymerization initiator optionally present as an adsorbate on the surface.

Advantageous Effects of Invention

According to the present invention, since a metal surface is treated by polymerizing a monomer in the presence of a hydrogen abstraction type photopolymerization initiator, a polymer derived from the monomer is consequently chemically bonded to the metal surface to impart lubricity to the metal surface, and further to improve the durability of the lubricant layer on the surface, thereby reducing deterioration of the sliding properties of the metal.

DESCRIPTION OF EMBODIMENTS

The surface-modified metal of the present invention has a surface at least partially treated by polymerizing a monomer in the presence of a hydrogen abstraction type photopolymerization initiator.

Lubricant layers on metal surfaces formed by conventional surface treatment or coating methods are not chemically bonded to the surfaces and are easily peeled or removed by a stress such as rubbing by a hand, friction with an object contacting the metal (e.g., a catheter or cells in the body when the metal is a guide wire), flows of chemicals or blood, or the like, and they are therefore disadvantageous in terms of maintaining durability and sliding properties. In contrast, in the surface-modified metal of the present invention, the surface treatment in which a monomer is polymerized in the presence of a hydrogen abstraction type photopolymerization initiator allows a polymer derived from the monomer to be chemically bonded to the metal surface. This inhibits peeling or removal of the lubricant layer on the metal surface due to a stress, friction, flows of a liquid, or the like, so that deterioration of the sliding properties of the metal can be reduced.

The surface-modified metal of the present invention has a surface treated by polymerizing a monomer in the presence of a hydrogen abstraction type photopolymerization initiator, at least at a potion where lubricity is required. The entire surface of the surface-modified metal may be treated as above.

Examples of the hydrogen abstraction type photopolymerization initiator include carbonyl compounds, organic sulfur compounds such as tetraethylthiuram disulfide, persulfides, redox compounds, azo compounds, diazo compounds, halogen compounds, and photoreducing dyes. Preferred among these are carbonyl compounds. These compounds may be used alone or in combinations of two or more as the hydrogen abstraction type photopolymerization initiator.

The carbonyl compound used as the photopolymerization initiator is preferably any of benzophenone and its derivatives. For example, benzophenone compounds represented by Formula (1) below can be suitably used.

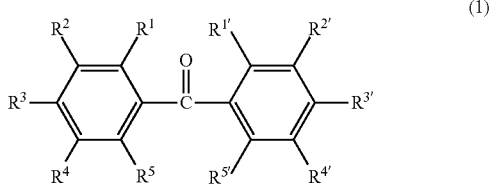

In Formula (1), $R^1$ to $R^5$ and $R^{1'}$ to $R^{5'}$ are the same as or different from one another, and each represent a hydrogen atom, an alkyl group, a halogen (fluorine, chlorine, bromine, iodine), a hydroxy group, a primary to tertiary amino group, a mercapto group, or a hydrocarbon group optionally containing an oxygen atom, a nitrogen atom, or a sulfur atom; and any adjacent two of them may be joined to each other to forma ring structure together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone because good polymer brushes can be formed.

Other examples of suitable benzophenone compounds include fluorobenzophenone compounds, such as 2,3,4,5,6-pentafluorobenzophenone and decafluorobenzophenone.

Thioxanthone compounds can also be suitably used as the polymerization initiator because they provide a high polymerization rate and also can easily be adsorbed on and/or reacted with metals. For example, compounds represented by Formula (2) below can be suitably used.

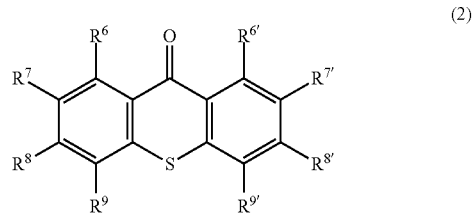

In Formula (2), $R^6$ to $R^9$ and $R^{6'}$ to $R^{9'}$ are the same as or different from one another, and each represent a hydrogen atom, a halogen atom, an alkyl group, a cyclic alkyl group, an aryl group, an alkenyl group, an alkoxy group, or an aryloxy group.

Examples of thioxanthone compounds represented by Formula (2) include thioxanthone, 2-isopropylthioxanthone, 4-isopropylthioxanthone, 2,3-dimethylthioxanthone, 2,4-dimethylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are compounds in which one or two, especially two of $R^6$ to $R^9$ and $R^{6'}$ to $R^{9'}$ are substituted with alkyl groups. More preferred is 2,4-diethylthioxanthone.

In the polymerization of a monomer in the presence of the hydrogen abstraction type photopolymerization initiator, the existence form of the photopolymerization initiator is not particularly limited as long as the monomer is polymerized in conditions where the photopolymerization initiator coexists with the monomer. Preferably, the photopolymerization initiator is present as an adsorbate on the surface of a metal.

The photopolymerization initiator may be adsorbed to the surface of a metal for example by, in the case of a benzophenone compound or a thioxanthone compound, treating a surface portion of a metal to be modified with a solution obtained by dissolving the benzophenone compound or thioxanthone compound in an organic solvent. This treatment allows the benzophenone compound or thioxanthone compound to be adsorbed on the metal surface so that, optionally after evaporating the organic solvent by drying, photopolymerization initiation points are formed. The surface may be treated by any method that allows the solution of the benzophenone compound or thioxanthone compound to be brought into contact with the metal surface. Suitable methods include, for example, application or spraying of the benzophenone or thioxanthone compound solution, and immersion into the solution. Moreover, if only part of the surface needs to be modified, it is sufficient to adsorb the photopolymerization initiator only to such part of the surface. In this case, for example, application or spraying of the solution is suitable.

Examples of the organic solvent include methanol, ethanol, acetone, benzene, toluene, methyl ethyl ketone, ethyl acetate, and THF. Preferred is acetone because it is rapidly dried and evaporated off.

In an exemplary preferred existence form of the photopolymerization initiator, the photopolymerization initiator is chemically bonded to the metal surface by, after adsorbing the benzophenone compound or thioxanthone compound on the metal surface by the above method, irradiating the adsorbed compound with light to chemically bond the benzophenone compound or thioxanthone compound to the metal surface. For example, the benzophenone compound or thioxanthone compound may be immobilized on the metal surface by irradiation with ultraviolet light having a wavelength of 250 to 450 nm, and preferably 250 to 400 nm. During the adsorption and immobilization of the photopolymerization initiator, hydrogen is abstracted from the hydroxy group on the metal surface and then the hydroxy group on the metal surface is covalently bonded to the carbon of C=O in the benzophenone compound or thioxanthone compound while the abstracted hydrogen is bonded to the oxygen of C=O to form C—O—H.

In an exemplary polymerization of a monomer in the presence of the hydrogen abstraction type photopolymerization initiator, the photopolymerization initiator adsorbed or chemically bonded to the metal surface abstracts hydrogen from the metal surface to generate a radical on the metal surface and, starting from this radical, a monomer is photopolymerized. In particular, the monomer is preferably photoradically polymerized by irradiation with light having a wavelength of 250 to 450 nm, and preferably 250 to 400 nm, to grow polymer chains on the metal surface.

In an exemplary method for the polymerization of a monomer, a (liquid) monomer or a solution thereof is applied or coated (sprayed) onto a metal surface where a hydrogen abstraction type photopolymerization initiator such as a benzophenone compound or a thioxanthone compound is adsorbed or chemically bonded, or the metal is immersed in a (liquid) monomer or a solution thereof, followed by irradiation with light. This allows the radical polymerization (photoradical polymerization) of the monomer to proceed so that polymer chains are grown on the metal surface. In another method, after the application, coating, spraying, or immersion, the metal surface may be covered with a transparent sheet of glass, PET, polycarbonate, or the like, followed by irradiating the covered surface with light.

The solvent for application (spraying), the method for application (spraying), the method for immersion, the conditions for irradiation, and the like may be conventionally known materials or methods. The solution of the monomer used is an aqueous solution or a solution in an organic solvent that hardly dissolves or does not dissolve the photopolymerization initiator used (e.g., a benzophenone compound). The (liquid) monomer or solution thereof used may contain a known polymerization inhibitor such as 4-methylphenol.

In the present invention, the radical polymerization of the monomer is allowed to proceed by light irradiation after the application of the (liquid) monomer or a solution thereof or after the immersion therein. Here, UV light sources with an emission wavelength mainly in the ultraviolet region, such as high-pressure mercury lamps, metal halide lamps, and LED lamps, can be suitably used. The light dose may be appropriately set in view of polymerization time and uniformity of the reaction progress. Moreover, in order to prevent inhibition of the polymerization due to active gas such as oxygen in the reaction vessel, it is preferable to remove oxygen from the reaction vessel and the reaction solution during or before light irradiation. Thus, for example, a method may appropriately be employed in which an inert gas such as nitrogen gas or argon gas is inserted into the reaction vessel and the reaction solution to discharge active gas such as oxygen from the reaction system and thereby replace the atmosphere in the reaction system with the inert gas. Oxygen may also be removed by vacuum deaeration. Moreover, in order to prevent inhibition of the reaction due to oxygen or the like, for example, a measure may appropriately be taken in which a UV light source is placed so that no air layer (oxygen content: 15% or higher) exists between the reaction vessel made of glass, plastics or the like and the reaction solution or the metal.

The light used for the polymerization of the monomer preferably has a wavelength of 250 to 450 nm and more preferably 250 to 400 nm. The light having such a wavelength allows polymer chains to be formed well on the metal surface. In contrast, UV light having a wavelength of less than 250 nm may have low ability to polymerize a monomer, while light having a wavelength of more than 450 nm may not easily activate the photopolymerization initiator, so that the polymerization reaction may be less likely to proceed. The light source may be a high-pressure mercury lamp, an LED with a center wavelength of 365 nm, an LED with a center wavelength of 375 nm, or the like. In particular, preferred is irradiation with LED light of 300 to 400 nm, more preferably LED light of 350 to 380 nm. Particularly, LEDs or the like which have a center wavelength of 365 nm, which is close to the excitation wavelength 366 nm of benzophenone, are preferred in view of efficiency.

Although LED light is suitable because it has a narrow wavelength range and does not have wavelengths other than the center wavelength, a mercury lamp or the like can produce the same effect as that of LED light if light smaller than 250 nm is blocked using a filter.

The irradiation time for the polymerization of the monomer is not particularly limited, and may be appropriately set in such a manner that the polymerization of the monomer proceeds sufficiently. In particular, the irradiation time is preferably 100 to 10000 minutes. The irradiation time within such a range allows polymer chains to be formed well on the metal surface. The irradiation time is more preferably 200 minutes or longer, still more preferably 300 minutes or longer, further preferably 1000 minutes or longer, and particularly preferably 1500 minutes or longer. The irradiation time is also more preferably 7000 minutes or shorter, still more preferably 5000 minutes or shorter, and particularly preferably 4500 minutes or shorter.

The monomer to be polymerized in the presence of the photopolymerization initiator is preferably at least one selected from the group consisting of hydrophilic monomers and metal salt-containing hydrophilic monomers. Examples of the hydrophilic monomer include hydrophilic monomers such as acrylamide and acrylonitrile, and ionic monomers having an ionic group in a substituent, a side chain or the like. Examples of the ionic monomer include monomers (cationic monomers) having a positive charge such as ammonium and phosphonium; and monomers (anionic monomers) having a negative charge, such as a sulfonic acid group, a carboxyl group, a phosphoric acid group, and a phosphonic acid group, or containing an acidic group that can be dissociated into a negatively charged group.

Specific examples of the ionic monomer include: acrylic acid, methacrylic acid, itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, styrenesulfonic acid, and amine salts of the foregoing; allylamine, 2-dimethylaminoethyl (meth)acrylate, and their hydrohalic acid salts; and 3-trimethylammonium propyl (meth)acrylate, 3-trimethylammonium propyl (meth)acrylamide, N,N,N-trimethyl-N-(2-hydroxy-3-methacryloyloxypropyl) ammonium chloride, and 2-(methacryloyloxy)ethyltrimethylammonium chloride (methacroylcholine chloride).

The hydrophilic monomer may be a zwitterionic monomer (zwitterionic group-containing compound: compound bearing a center of permanent positive charge and a center of negative charge) such as a carboxybetaine, sulfobetaine, or phosphobetaine. The zwitterionic monomer may be a compound represented by Formula (3) below and particularly suitably a compound represented by Formula (4) below because then excellent sliding properties and excellent durability can be achieved.

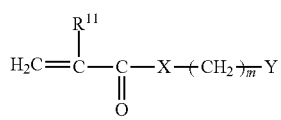
(3)

In Formula (3), $R^{11}$ represents —H or —CH$_3$; X represents —O— or —NH—; m represents an integer of 1 or more; and Y represents a zwitterionic group.

In Formula (3), preferably, $R^{11}$ is —CH$_3$, X is —O—, and m is 1 to 10. In the zwitterionic group designated by Y, the cation may be a quaternary ammonium such as tetraalkylammonium, and the anion may be a carboxylic acid, sulfonic acid, phosphate or the like.

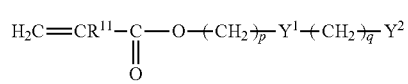
(4)

In Formula (4), $R^{11}$ represents —H or —CH$_3$; p and q each represent an integer of 1 or more; and $Y^1$ and $Y^2$ represent ionic functional groups having charges opposite to each other.

In Formula (4), p is preferably an integer of 2 or more, and more preferably an integer of 2 to 10, and q is preferably an integer of 1 to 10, and more preferably an integer of 2 to 4. Moreover, $R^{11}$ is preferably defined as above. $Y^1$ and $Y^2$ are as defined for the cation and anion above.

Typical suitable examples of the zwitterionic monomer include compounds represented by the following Formulae (4-1) to (4-4).

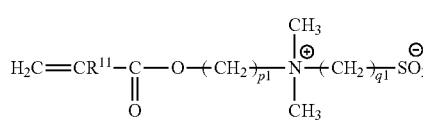
(4-1)

In Formula (4-1), $R^{11}$ represents a hydrogen atom or a methyl group, and p1 and q1 each represent an integer of 1 to 10.

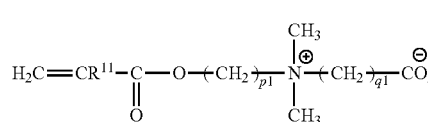
(4-2)

In Formula (4-2), $R^{11}$ represents a hydrogen atom or a methyl group, and p1 and q1 each represent an integer of 1 to 10.

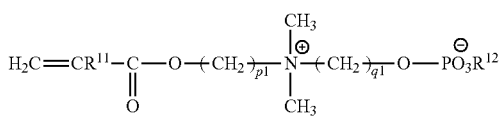
(4-3)

In Formula (4-3), $R^{11}$ represents a hydrogen atom or a methyl group, $R^{12}$ represents a C1-C6 hydrocarbon group, and p1 and q1 each represent an integer of 1 to 10.

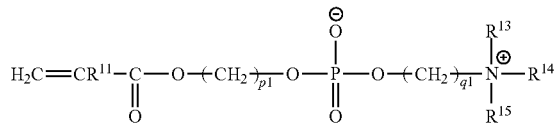
(4-4)

In Formula (4-4), $R^{11}$ represents a hydrogen atom or a methyl group; $R^{13}$, $R^{14}$, and $R^{15}$ are the same as or different from one another and each represent a C1 or C2 hydrocarbon group; and p1 and q1 each represent an integer of 1 to 10.

Examples of the compound represented by Formula (4-1) include dimethyl(3-sulfopropyl)(2-(meth)acryloyloxyethyl) ammonium betaine and [2-(methacryloyloxy)ethyl]dimethyl (3-sulfopropyl)aminium hydroxide. Examples of the compound represented by Formula (4-2) include dimethyl(2-carboxyethyl)-(2-(meth)acryloyloxyethyl)ammonium betaine. Examples of the compound represented by Formula (4-3) include dimethyl(3-methoxyphosphopropyl)-(2-(meth)acryloyloxyethyl)ammonium betaine. Examples of the compound represented by Formula (4-4) include 2-(meth)acryloyloxyethyl phosphorylcholine.

Examples of the metal salt-containing hydrophilic monomer include metal salts of acids such as acrylic acid, methacrylic acid, itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, and styrenesulfonic acid.

The metal salt is preferably an alkali metal salt, such as sodium or potassium, or an alkaline earth metal salt, such as calcium.

When the monomer used is a hydrophilic monomer containing a carboxylic acid such as acrylic acid or methacrylic acid, it may be converted to a metal salt using sodium hydroxide, potassium hydroxide, sodium hydrogen carbonate or the like after the polymerization reaction.

In particular, the monomer is particularly preferably at least one selected from the group consisting of acrylic acid, acrylic acid metal salts, methacrylic acid, methacrylic acid metal salts, 3-sulfopropyl methacrylate potassium salt, 2-(methacryloyloxy)ethyltrimethylammonium chloride, 2-methacryloyloxyethyl phosphorylcholine, and [2-(methacryloyloxy)ethyl]dimethyl(3-sulfopropyl)aminium hydroxide, because then particularly excellent sliding properties and particularly excellent durability can be achieved.

For excellent sliding properties and excellent durability, polymer chains represented by any of Formulae (5) to (7) below are preferably formed in the polymerization of the monomer. Such formed polymer chains also provide prevention of adsorption or aggregation of proteins.

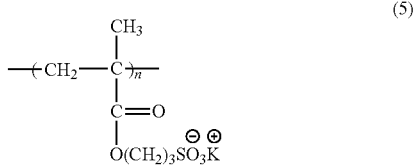

(5)

wherein n represents an integer of 1 or more.

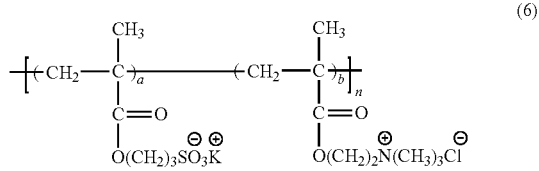

(6)

wherein n represents an integer of 1 or more, and 5≤a/b≤200.

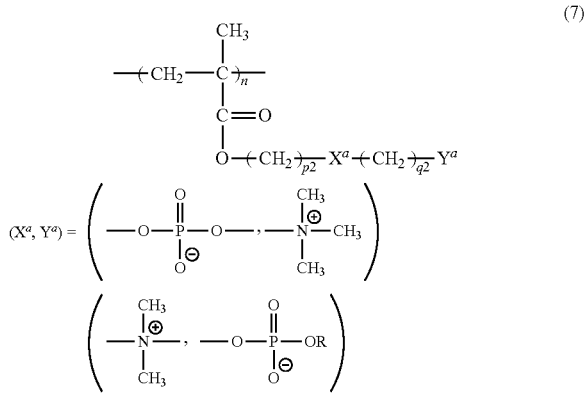

(7)

wherein n represents an integer of 1 or more; p2≥2; q2=2, 3, or 4; and R represents a hydrocarbon group.

In Formulae (5) to (7), n (polymerization degree) is preferably 20 to 200000, and more preferably 350 to 50000. If n is less than 20, the polymer chains are so short that they may be concealed by irregularities on the metal surface, which tends to result in failure to provide sliding properties. If n is more than 200000, the amount of monomer used is increased, which tends to result in an economic disadvantage. Moreover, examples of the hydrocarbon group for R include a methyl group and an ethyl group.

The length of the formed polymer chain is preferably 10 to 50000 nm, and more preferably 100 to 50000 nm. If the length is shorter than 10 nm, good sliding properties tend not to be achieved. If the length is longer than 50000 nm, a further improvement in sliding properties cannot be expected while the cost of raw materials tends to increase due to the use of the expensive monomer. In addition, surface patterns generated by the surface treatment tend to be visible to the naked eyes and thereby spoil the appearance.

In the polymerization of the monomer, one kind of monomer or two or more kinds of monomers may be radically polymerized starting from the polymerization initiation points. Moreover, multiple kinds of polymer chains may be grown on the metal surface.

In the surface-modified metal of the present invention, the polymer chains formed by polymerization of the monomer may be cross-linked to one another. In this case, the polymer chains may be cross-linked by ionic cross-linking, or cross-linking by a hydrophilic group containing an oxygen atom. Moreover, in the polymerization of the monomer, a slight amount of a compound having at least two vinyl groups in a molecule may be added to introduce crosslinks between the polymer chains during the polymerization.

The compound having at least two vinyl groups in a molecule may suitably be N,N'-methylenebisacrylamide or the like.

The surface-modified metal of the present invention, which has a surface at least partially treated by polymerizing a monomer in the presence of a hydrogen abstraction type photopolymerization initiator, is preferably treated with a silane coupling agent prior to the polymerization of the monomer in the presence of the hydrogen abstraction type photopolymerization initiator. Thus, in another suitable embodiment of the present invention, the surface of the surface-modified metal is treated with a silane coupling agent prior to polymerizing the monomer in the presence of the hydrogen abstraction type photopolymerization initiator. As a result of the treatment with a silane coupling agent prior to the polymerization of the monomer in the presence of the hydrogen abstraction type photopolymerization initiator, the polymer is chemically bonded to the metal via the silane coupling agent, so that a stronger bond is formed and leads to a further enhancement of the sliding properties and durability of the surface-modified metal.

The silane coupling agent is not particularly limited. For example, it is preferably a vinyl group-containing compound containing a hydrolyzable group and a vinyl group because hydrogen can be easily abstracted. Such a vinyl group-containing compound can react with and bond to a hydroxy group present on the metal surface via the hydrolyzable group, and its vinyl group can form a polymerization initiation point for the monomer. Consequently, polymer chains grown starting from the polymerization initiation points are chemically bonded to the metal via the silane coupling agent. More preferred as the silane coupling agent are vinyltrimethoxysilane, vinyltriethoxysilane, (3-acryloyloxypropyl)trimethoxysilane, (3-acryloyloxypropyl)triethoxysilane, (3-methacryloyloxypropyl)trimethoxysilane, (3-methacryloyloxypropyl)triethoxysilane, vinylchlorodimethylsilane, (3-acryloyloxypropyl)chlorodimethylsilane, and (3-methacryloyloxypropyl)chlorodimethylsilane. Still more preferred are (3-acryloyloxypropyl)trimethoxysilane, (3-acryloyloxypropyl)triethoxysilane, and (3-acryloyloxypropyl)chlorodimethylsilane. In view of reactivity and safety, particularly preferred is (3-acryloyloxypropyl)trimethoxysilane.

The treatment with the silane coupling agent may be carried out by coating methods such as by application, spraying, immersion, or the like. The treatment is preferably carried out by preparing the silane coupling agent (silane compound) into an aqueous solution, alcohol solution, acetone solution or the like beforehand, and then coating it onto the metal surface, followed either by drying by heat, or leaving under moisture in the air, under wet conditions or the like to cause hydrolysis and dehydration condensation. Thus, a chemical bond is formed between the hydroxy group on the metal surface and the silane coupling agent (silane compound), so that they are fixed to each other. The drying temperature and time may be appropriately set, for example, to a temperature and time capable of forming a chemical bond. The drying temperature is preferably 40° C. to 150° C.

In the preparation of an aqueous solution, additional treatment may be performed as appropriate such as by adding alcohol to prepare a mixed water/alcohol solution, or by adjusting the pH to weakly acidic with acetic acid or the like. Such treatment may be performed as appropriate because the solubility of the silane coupling agent in water varies depending on the kind of silane coupling agent.

When the treatment with the silane coupling agent is carried out before the polymerization of the monomer in the presence of the hydrogen abstraction type photopolymerization initiator, the monomer is polymerized in the presence of the above-described hydrogen abstraction type photopolymerization initiator after the treatment with the silane coupling agent. In other words, a radical is generated from the hydrocarbon group of the silane coupling agent, such as vinyl, acrylate, or methacrylate group, by using the hydrogen abstraction type photopolymerization initiator and, starting from this radical, surface-initiated radical polymerization is carried out to polymerize the monomer. Thus, a polymer formed from the monomer is chemically bonded to the metal surface via the silane coupling agent, which reduces deterioration of sliding properties due to friction, rubbing, or flows.

Moreover, the surface-modified metal of the present invention is preferably obtained by polymerizing the monomer in the presence of the hydrogen abstraction type photopolymerization initiator, followed by further treatment by polymerizing a monomer at least once in the presence of a hydrogen abstraction type photopolymerization initiator optionally present as an adsorbate on the surface.

In the case of performing, after polymerizing the monomer in the presence of the hydrogen abstraction type photopolymerization initiator, further treatment by polymerizing a monomer at least once in the presence of a hydrogen abstraction type photopolymerization initiator optionally present as an adsorbate on the surface, after the polymerization of the monomer in the presence of the hydrogen abstraction type photopolymerization initiator as described above, polymerization of a monomer is performed again at least once in the presence of a hydrogen abstraction type photopolymerization initiator optionally present as an adsorbate on the surface. This means that the treatment of polymerizing a monomer in the presence of a hydrogen abstraction type photopolymerization initiator is carried out at least twice. As a result of such treatment, polymer layers are stacked on the metal surface, so that the sliding properties of the resulting surface-modified metal can be further enhanced.

The method for polymerizing a monomer in the second and subsequent treatments is the same as that in the first treatment described above. When the treatment of polymerizing a monomer in the presence of a hydrogen abstraction type photopolymerization initiator is carried out at least twice as mentioned above, it is preferable to perform, prior to the polymerization of a monomer in the (k+1)th treatment, treatment with a hydrogen abstraction type photopolymerization initiator, and then polymerize a monomer in the (k+1)th treatment. After the polymerization of a monomer in the k-th treatment, polymerization of a monomer may be directly subsequently performed in the (k+1)th treatment. Or, after the polymerization of a monomer in the k-th treatment, unreacted monomer and the like may once be washed away from the surface of the resulting surface-modified metal by washing with water, drying and the like, followed by polymerization of a monomer in the (k+1)th treatment. Here, the existence form of the hydrogen abstraction type photopolymerization initiator used in the polymerization of a monomer in the (k+1)th treatment, the method for the treatment with the hydrogen abstraction type photopolymerization initiator prior to the polymerization of a monomer in the (k+1)th treatment, and the kind of hydrogen abstraction type photopolymerization initiator used are as described above.

It is to be noted that "k" in the present paragraph represents an integer of 1 or more.

Moreover, in the treatment method, the monomer used in the first treatment and the monomers used in the second or subsequent treatment may be the same as or different from each other. Furthermore, when the number of second and subsequent treatments is more than one, the monomers used in the plurality of treatments may be the same as or different from each other.

Particularly from the economical standpoint, when the treatment of polymerizing a monomer is performed n times (n is an integer of 2 or more), it is more preferable to use in the first to (n−1)th treatments relatively inexpensive monomers such as acrylic acid, acrylamide, and acrylonitrile, and in the n-th treatment the aforementioned zwitterionic monomer such as 2-(meth)acryloyloxyethyl phosphorylcholine, or [2-(methacryloyloxy)ethyl]dimethyl(3-sulfopropyl) aminium hydroxide, the aforementioned metal salt-containing hydrophilic monomer such as a metal salt of an acid such as 3-sulfopropyl (meth)acrylate, or a halide monomer such as methacroylcholine chloride because then sliding properties are further improved even as compared to when, for example, the metal salt-containing hydrophilic monomer is used for n times.

Thus, in another suitable embodiment of the present invention, the surface-modified metal is obtained by polymerizing at least one monomer selected from the group consisting of acrylic acid, acrylamide, and acrylonitrile in the presence of the hydrogen abstraction type photopolymerization initiator, followed by further treatment by polymerizing at least one monomer selected from the group consisting of 2-(meth)acryloyloxyethyl phosphorylcholine, 3-sulfopropyl (meth)acrylate potassium salt, [2-(methacryloyloxy)ethyl]dimethyl(3-sulfopropyl)aminium hydroxide, and methacroylcholine chloride at least once in the presence of a hydrogen abstraction type photopolymerization initiator optionally present as an adsorbate on the surface.

As described above, the surface-modified metal of the present invention is obtained by forming polymerization initiation points on the surface of a metal using a hydrogen abstraction type photopolymerization initiator, and polymerizing a monomer starting from the polymerization initiation points to grow polymer chains on the metal surface.

Thus, the present invention also encompasses a method for modifying a metal surface, including the step of growing polymer chains on the metal surface by polymerizing a monomer in the presence of a hydrogen abstraction type photopolymerization initiator on the metal surface.

In the above step, first, polymerization initiation points are formed on the surface of a metal. This can be accomplished, for example, by adsorbing the aforementioned photopolymerization initiator on the metal surface to form polymerization initiation points or by adsorbing the photopolymerization initiator on the metal surface, and then immobilizing the photopolymerization initiator on the surface by irradiation with UV light of 250 to 450 nm, to form polymerization initiation points.

The hydrogen abstraction type photopolymerization initiator is as described above. The method for adsorbing the photopolymerization initiator on the metal surface and the method for irradiation with UV light are also as described above.

In the above step, a monomer is polymerized (radically polymerized) starting from the polymerization initiation points to grow polymer chains on the metal surface. The kind of monomer and the polymerization method are as described above.

The method for modifying a metal surface may further include, prior to the above step, the step of reacting a metal with a silane coupling agent to bond the silane coupling agent to the metal surface. Thus, in another suitable embodiment of the present invention, the method for modifying a metal surface includes the step of treating the metal surface with a silane coupling agent prior to the step of growing polymer chains.

The kind of silane coupling agent and the method for reacting the metal and the silane coupling agent are as described above.

Moreover, the method for modifying a metal surface may further include, after the step of growing polymer chains, the step of polymerizing a monomer at least once in the presence of a hydrogen abstraction type photopolymerization initiator optionally present as an adsorbate on the surface. Repeating at least twice the step of polymerizing a monomer in the presence of a hydrogen abstraction type photopolymerization initiator as described above allows the surface-modified metal to have more improved sliding properties. The method for repeating at least twice the treatment of polymerizing a monomer in the presence of a hydrogen abstraction type photopolymerization initiator, the kind of monomer used, the existence form of the hydrogen abstraction type photopolymerization initiator, the method for treatment with the hydrogen abstraction type photopolymerization initiator, and the kind of hydrogen abstraction type photopolymerization initiator used are as described above.

Exemplary materials of the surface-modified metal of the present invention include metals such as stainless steel, nickel-titanium alloys, iron, titanium, aluminum, tin, and zinc-tungsten alloys. Among these, stainless steel and nickel-titanium alloys are preferred in view of bonding between the metal surface and the lubricant layer and biocompatibility. Thus, in another suitable embodiment of the present invention, the surface-modified metal of the present invention includes stainless steel or a nickel-titanium alloy.

The surface-modified metal of the present invention has a metal surface which is imparted with lubricity and further on which the lubricant layer has improved durability to reduce deterioration of the sliding properties of the metal. Such a metal can be suitably used for example for metal medical devices, e.g., guide wires, syringe needles, metal tubes in medical devices or equipment and other medical devices. Thus, the present invention also encompasses a medical device including the surface-modified metal. In another suitable embodiment of the present invention, the medical device is a guide wire, a syringe needle, or a tube of a medical instrument.

Moreover, by applying the modification method to at least part of a three-dimensional metal, a surface-modified three-dimensional metal can be obtained. Further, preferred examples of such a metal include polymer brushes. The polymer brush as used herein refers to an assembly of graft polymer molecules obtained in the "grafting from" approach by surface-initiated living radical polymerization. The graft chains are preferably oriented in a direction substantially vertical to the metal surface because then entropy is reduced and thus the molecular mobility of the graft chains is reduced to provide sliding properties. Furthermore, semidilute or concentrated brushes which have a brush density of 0.01 chains/nm$^2$ or higher are preferred.

EXAMPLES

The present invention is more specifically described by reference to examples below but is not limited only to these examples.

Example 1

The surface of a SUS flat plate (10 cm square, 1 mm in thickness) was washed with acetone and then dried.

The plate was immersed in a 2% by mass aqueous solution of (3-acryloyloxypropyl)trimethoxysilane (with 2% by mass of acetic acid) for 10 minutes, and then taken out from the solution and dried for 24 hours. The plate was then washed with acetone. The thus treated SUS plate was immersed in a 1% by mass solution of benzophenone in acetone, taken out and dried.

A 1.25 M aqueous solution of 3-sulfopropyl methacrylate potassium salt was dropped on the surface of the resulting SUS plate, and a glass plate with a thickness of 1 mm was placed thereon. The surface covered with the glass plate was irradiated with LED-UV (5 mW/cm$^2$) having a wavelength of 365 nm for 330 minutes to cause surface-initiated radical polymerization. The surface was then washed with water to wash away unreacted monomer and the like. In this manner, a surface-modified metal was obtained. The surface-modified metal was subjected to evaluation of sliding properties as described later.

Example 2

Treatment with a silane coupling agent, benzophenone treatment, and drying were performed in the same manner as in Example 1, except that the SUS plate was changed to a SUS guide wire (core wire).

Then, the resulting guide wire was put in a glass vessel containing a 1.25 M aqueous solution of 3-sulfopropyl methacrylate potassium salt, and the vessel was covered with a lid. The vessel was purged with argon for two hours to remove oxygen. The glass vessel was then irradiated with LED-UV (5 mW/cm$^2$) for 330 minutes while being rotated, to cause surface-initiated radical polymerization. In this manner, a. Surface-modified metal was obtained. The surface-modified metal was subjected to evaluation of sliding properties as described later.

Example 3

A surface-modified metal was obtained by surface-initiated radical polymerization carried out in the same manner as in Example 2, except that the SUS guide wire (core wire) was changed to a nickel-titanium alloy guide wire. The surface-modified metal was subjected to evaluation of sliding properties as described later.

Example 4

A surface-modified metal was obtained by surface-initiated radical polymerization carried out in the same manner as in Example 1, except that the treatment with a silane coupling agent was not performed. The surface-modified metal was subjected to evaluation of sliding properties as described later.

Example 5

A surface-modified metal was obtained by surface-initiated radical polymerization carried out in the same manner as in Example 2, except that the time for irradiation with LED-UV (5 mW/cm$^2$) was changed to 1800 minutes. The surface-modified metal was subjected to evaluation of sliding properties as described later.

Example 6

A surface-modified metal was obtained by surface-initiated radical polymerization carried out in the same manner as in Example 2, except that the time for irradiation with LED-UV (5 mW/cm$^2$) was changed to 4380 minutes. The surface-modified metal was subjected to evaluation of sliding properties as described later.

Example 7

The surface of a SUS guide wire (core wire) was washed with acetone and dried.

The guide wire was immersed in a 2% by mass aqueous solution of (3-acryloyloxypropyl)trimethoxysilane (with 2% by mass of acetic acid) for 10 minutes, and then taken out and dried for 24 hours. Then, the guide wire was washed with acetone. The thus treated SUS guide wire was immersed in a 1% by mass solution of benzophenone in acetone, taken out and dried.

The resulting SUS guide wire was put in a glass vessel containing a 2.5 M aqueous solution of acrylic acid, and the vessel was covered with a lid. The vessel was purged with argon for two hours to remove oxygen. The glass vessel was then irradiated with LED-UV (5 mW/cm$^2$) having a wavelength of 365 nm for 240 minutes while being rotated, to cause surface-initiated radical polymerization. Then, after the surface was washed with water and dried, the guide wire was immersed in a 1% by mass solution of benzophenone in acetone, taken out and dried. Subsequently, the guide wire was put in a glass vessel containing a 1.25 M aqueous solution of 3-sulfopropyl methacrylate potassium salt, and the vessel was covered with a lid and purged with argon for two hours to remove oxygen. The glass vessel was then irradiated with LED-UV (5 mW/cm$^2$) having a wavelength of 365 nm for 1800 minutes while being rotated, to cause surface-initiated radical polymerization. After that, the surface was washed with water to wash away unreacted monomer and the like. In this manner, a surface-modified metal was obtained. The surface-modified metal was subjected to evaluation of sliding properties as described later.

Example 8

The surface of a SUS guide wire (core wire) was washed with acetone and dried.

The guide wire was immersed in a 2% by mass aqueous solution of (3-acryloyloxypropyl)trimethoxysilane (with 2% by mass of acetic acid) for 10 minutes, and then taken out and dried for 24 hours. Then, the guide wire was washed with acetone. The thus treated SUS guide wire was immersed in a 1% by mass solution of benzophenone in acetone, taken out and dried.

The resulting SUS guide wire was put in a glass vessel containing a 2.5 M aqueous solution of acrylic acid, and the vessel was covered with a lid and purged with argon for two hours to remove oxygen. The glass vessel was then irradiated with LED-UV (5 mW/cm$^2$) having a wavelength of 365 nm for 240 minutes while being rotated, to cause surface-initiated radical polymerization. Then, after the surface was washed with water and dried, the guide wire was immersed in a 1% by mass solution of benzophenone in acetone, taken out and dried. Subsequently, the guide wire was put in a glass vessel containing a 1.25 M aqueous solution of 2-methacryloyloxyethyl phosphorylcholine, and the vessel was covered with a lid and purged with argon for two hours to remove oxygen. The glass vessel was then irradiated with LED-UV (5 mW/cm$^2$) having a wavelength of 365 nm for 1800 minutes while being rotated, to cause surface-initiated radical polymerization. After that, the surface was washed with water to wash away unreacted monomer and the like. In this manner, a surface-modified metal was obtained. The surface-modified metal was subjected to evaluation of sliding properties as described later.

Example 9

The surface of a SUS guide wire (core wire) was washed with acetone and dried.

The guide wire was immersed in a 2% by mass aqueous solution of (3-acryloyloxypropyl)trimethoxysilane (with 2% by mass of acetic acid) for 10 minutes, and then taken out and dried for 24 hours. The guide wire was then washed with acetone. The thus treated SUS guide wire was immersed in a 1% by mass solution of benzophenone in acetone, taken out and dried.

The resulting SUS guide wire was put in a glass vessel containing a 2.5 M aqueous solution of acrylamide, and the vessel was covered with a lid and purged with argon for two hours to remove oxygen. The glass vessel was then irradiated with LED-UV (5 mW/cm$^2$) having a wavelength of 365 nm for 240 minutes while being rotated, to cause surface-initiated radical polymerization. Then, after the surface was washed with water and dried, the guide wire was immersed in a 1% by mass solution of benzophenone in acetone, taken out and dried. Subsequently, the guide wire was put in a glass vessel containing a 1.25 M aqueous solution of 2-methacryloyloxyethyl phosphorylcholine, and the vessel was covered with a lid and purged with argon for two hours to remove oxygen. The glass vessel was then irradiated with LED-UV (5 mW/cm$^2$) having a wavelength of 365 nm for 1800 minutes while being rotated, to cause surface-initiated radical polymerization. After that, the surface was washed with water to wash away unreacted monomer and the like. In this manner, a surface-modified metal was obtained. The surface-modified metal was subjected to evaluation of sliding properties as described later.

Example 10

The surface of a SUS guide wire (core wire) was washed with acetone and dried.

The guide wire was immersed in a 2% by mass aqueous solution of (3-acryloyloxypropyl)trimethoxysilane (with 2% by mass of acetic acid) for 10 minutes, and then taken out and dried for 24 hours. Then, the guide wire was washed with acetone. The thus treated SUS guide wire was immersed in a 1% by mass solution of benzophenone in acetone, taken out and dried.

The resulting SUS guide wire was put in a glass vessel containing a 2.5 M aqueous solution of acrylic acid, and the vessel was covered with a lid and purged with argon for two hours to remove oxygen. The glass vessel was then irradiated with LED-UV (5 mW/cm$^2$) having a wavelength of 365 nm for 240 minutes while being rotated, to cause surface-initiated radical polymerization. Then, after the surface was washed with water and dried, the guide wire was immersed in a 1% by mass solution of benzophenone in acetone, taken out and dried. Subsequently, the guide wire was put in a glass vessel containing a 1.25 M aqueous solution of [2-(methacryloyloxy)ethyl]dimethyl (3-sulfopropyl) aminium hydroxide, and the vessel was covered with a lid and purged with argon for two hours to remove oxygen. The glass vessel was then irradiated with LED-UV (5 mW/cm$^2$) having a wavelength of 365 nm for 1800 minutes while being rotated, to cause surface-initiated radical polymerization. After that, the surface was washed with water to wash away unreacted monomer and the like. In this manner, a surface-modified metal was obtained. The surface-modified metal was subjected to evaluation of sliding properties as described later.

Example 11

The surface of a SUS guide wire (core wire) was washed with acetone and dried.

The guide wire was immersed in a 2% by mass aqueous solution of (3-acryloyloxypropyl)trimethoxysilane (with 2% by mass of acetic acid) for 10 minutes, and then taken out and dried for 24 hours. Then, the guide wire was washed with acetone. The thus treated SUS guide wire was immersed in a 1% by mass solution of benzophenone in acetone, taken out and dried.

The resulting SUS guide wire was put in a glass vessel containing a 2.5 M aqueous solution of acrylic acid, and the vessel was covered with a lid and purged with argon for two hours to remove oxygen. The glass vessel was then irradiated with LED-UV (5 mW/cm$^2$) having a wavelength of 365 nm for 240 minutes while being rotated, to cause surface-initiated radical polymerization. Then, after the surface was washed with water and dried, the guide wire was immersed in a 1% by mass solution of benzophenone in acetone, taken out and dried. Subsequently, the guide wire was put in a glass vessel containing a 1.25 M aqueous solution of 2-(methacryloyloxy)ethyltrimethyl-ammonium chloride, and the vessel was covered with a lid and purged with argon for two hours to remove oxygen. The glass vessel was then irradiated with LED-UV (5 mW/cm$^2$) having a wavelength of 365 nm for 1800 minutes while being rotated, to cause surface-initiated radical polymerization. After that, the surface was washed with water to wash away unreacted monomer and the like. In this manner, a surface-modified metal was obtained. The surface-modified metal was subjected to evaluation of sliding properties as described later.

Comparative Example 1

The surface of a SUS flat plate (10 cm square, 1 mm in thickness) was washed with acetone and dried, followed by evaluation of sliding properties as described later.

Comparative Example 2

A SUS guide wire (core wire) was only washed with acetone and dried, followed by evaluation of sliding properties as described later.

Comparative Example 3

A nickel-titanium alloy guide wire (core wire) was only washed with acetone and dried, followed by evaluation of sliding properties as described later.

Evaluation of Sliding Properties

The surface-treated metal, flat plate, or guide wire was watered and rubbed by a hand to evaluate sliding properties.

As a result of the evaluation, the surfaces of Comparative Examples 1, 2, and 3 were found not to be slippery but to have a feel like their original metal surface and thus have low sliding properties. When compared to these surfaces, the surfaces of Examples 1, 2, and 3 were slippery and had significantly improved sliding properties. The surface of Example 4 was slippery though it was less slippery than the surface of Example 1, and the surface of Example 4 had improved sliding properties as compared to Comparative Example 1. The surfaces of Examples 5 and 6 were more slippery than the surface of Example 2. Further, the surfaces of Examples 7, 8, 9, 10, and 11 were more slippery than the surfaces of Examples 5 and 6.

Moreover, the surfaces of Examples 1, 2, 3, 5, 6, 7, 8, 9, 10, and 11 remained slippery even after rubbing 100 times, and the sliding properties were not changed. The surface of Example 4 was also rubbed 100 times, and its initial sliding properties were not changed even after rubbing 100 times.

The invention claimed is:

1. A method for producing a guide wire, a syringe needle, or a tube of a medical instrument comprising a modified metal surface, the method comprising:
    treating the metal surface of the guide wire, syringe needle, or tube of a medical instrument with a silane coupling agent to form a treated metal surface;
    followed by growing polymer chains on the treated metal surface by polymerizing a monomer which is exposed to irradiation with light having a wavelength of 250 to 450 nm for a time period of 100 to 10000 minutes in the presence of a hydrogen abstraction type photopolymerization initiator on the treated metal surface,
    wherein the monomer is at least one selected from the group consisting of acrylamide, ionic monomer, zwitterionic monomer, and metal salt-containing hydrophilic monomer, and
    wherein the silane coupling agent is at least one selected from the group consisting of vinyltrimethoxysilane, vinyltriethoxysilane, (3-acryloyloxypropyl)trimethoxysilane, (3-acryloyloxypropyl)triethoxysilane, (3-methacryloyloxypropyl)trimethoxysilane, (3-methacryloyloxypropyl)triethoxysilane, vinylchlorodimethylsilane, (3-acryloyloxypropyl)chlorodimethylsilane, and (3-methacryloyloxypropyl)chlorodimethylsilane.

2. The method for producing a guide wire, a syringe needle, or a tube of a medical instrument according to claim 1, further comprising, after the step of growing polymer chains, the step of polymerizing a monomer at least once in the presence of a hydrogen abstraction type photopolymerization initiator or in the presence of a hydrogen abstraction type photopolymerization initiator adsorbed to the surface.

3. A method for producing a guide wire, a syringe needle, or a tube of a medical instrument, comprising a modified metal surface,
    wherein the modified metal surface is obtained by polymerizing on the metal surface of the guide wire, syringe needle, or tube of a medical instrument at least a first monomer selected from the group consisting of acrylic acid, acrylamide, and acrylonitrile by exposing the first monomer to irradiation with light having a wavelength of 250 to 450 nm for a time period of 100 to 10000 minutes in the presence of a hydrogen abstraction type photopolymerization initiator in order to produce a first modified metal surface, followed by further treatment of the first modified metal surface by polymerizing at least a second monomer selected from the group consisting of
2-(meth)acryloyloxyethyl phosphorylcholine,
3-sulfopropyl (meth)acrylate potassium salt,
[2-(methacryloyloxy)ethyl]dimethyl(3-sulfopropyl) aminium hydroxide, and methacroylcholine chloride
at least once by exposing the second monomer to irradiation with light having a wavelength of 250 to 450 nm for a time period of 100 to 10000 minutes in the presence of a hydrogen abstraction type photopolymerization initiator or in the presence of a hydrogen abstraction type photopolymerization initiator adsorbed to the surface.

* * * * *